(12) United States Patent
Vandegriff et al.

(10) Patent No.: US 10,029,001 B2
(45) Date of Patent: Jul. 24, 2018

(54) DIASPIRIN CROSSLINKED PEGYLATED HEMOGLOBIN

(71) Applicant: William Schindler, Santa Fe, NM (US)

(72) Inventors: Kim D. Vandegriff, Santa Fe, NM (US); Ashok Malavalli, San Diego, CA (US); Scott D. Olsen, La Jolla, CA (US)

(73) Assignee: William Schindler, Santa Fe, NM (US)

( * ) Notice: Subject to any disclaimer, the term of this patent is extended or adjusted under 35 U.S.C. 154(b) by 0 days.

(21) Appl. No.: 14/388,956

(22) PCT Filed: Mar. 15, 2013

(86) PCT No.: PCT/US2013/032694
§ 371 (c)(1),
(2) Date: Sep. 29, 2014

(87) PCT Pub. No.: WO2013/148375
PCT Pub. Date: Oct. 3, 2013

(65) Prior Publication Data
US 2015/0087590 A1 Mar. 26, 2015

Related U.S. Application Data

(60) Provisional application No. 61/617,639, filed on Mar. 29, 2012.

(51) Int. Cl.
| *A61K 38/42* | (2006.01) |
| *A61K 47/48* | (2006.01) |
| *C07K 14/805* | (2006.01) |
| *C12N 9/06* | (2006.01) |
| *C07K 1/10* | (2006.01) |
| *C04B 35/634* | (2006.01) |

(52) U.S. Cl.
CPC ........ *A61K 38/42* (2013.01); *A61K 47/48215* (2013.01); *C07K 1/10* (2013.01); *C07K 14/805* (2013.01); *C12N 9/0044* (2013.01); *C04B 35/63488* (2013.01); *Y10T 436/105831* (2015.01)

(58) Field of Classification Search
None
See application file for complete search history.

(56) References Cited

U.S. PATENT DOCUMENTS

| 5,234,903 | A | 8/1993 | Nho et al. |
| 5,296,465 | A | 3/1994 | Rausch et al. |
| 5,585,484 | A | 12/1996 | Acharya et al. |
| 5,750,725 | A | 5/1998 | Acharya et al. |
| 6,017,943 | A | 1/2000 | Acharya et al. |
| 6,627,738 | B2 | 9/2003 | Stamler et al. |
| 6,828,401 | B2 | 12/2004 | Nho et al. |
| 6,844,317 | B2 | 1/2005 | Winslow et al. |
| 7,144,989 | B2 | 12/2006 | Acharya et al. |
| 7,169,900 | B2 | 1/2007 | Acharya et al. |
| 7,501,499 | B2 | 3/2009 | Acharya et al. |
| 7,989,414 | B2 * | 8/2011 | Winslow ................ A61K 38/42 424/1.69 |
| 9,138,464 | B2 * | 9/2015 | Winslow ................ A61K 33/00 |
| 9,241,979 | B2 * | 1/2016 | Winslow ................ A61K 38/42 |
| 2005/0164915 | A1 * | 7/2005 | Winslow ................ A61K 38/42 514/13.4 |
| 2006/0234915 | A1 | 10/2006 | Winslow |
| 2009/0298746 | A1 | 12/2009 | Acharya et al. |

FOREIGN PATENT DOCUMENTS

| WO | 03/059363 A1 | 7/2003 |
| WO | 2011/106396 A1 | 9/2011 |

OTHER PUBLICATIONS

Walder et al. Diaspirins that cross-link beta chains of hemoglobin: bis(3,5-dibromosalicyl) succinate and bis(3,5-dibromosalicyl) fumarate. Biochemistry. Oct. 2, 1979;18(20):4265-70.*
Vandegriff et al. MP4, a new nonvasoactive PEG-Hb conjugate. Transfusion 2003; 43:509-516.*
Gladwin et al. The functional nitrite reductase activity of the heme-globins. Blood. Oct. 1, 2008;112(7):2636-47.*
Lui et al. Polyethylene Glycol Conjugation Enhances the Nitrite Reductase Activity of Native and Cross-Linked Hemoglobin. Biochemistry 2008, 47, 10773-10780.*
Manjula et al. Cys-93-bb-Succinimidophenyl Polyethylene Glycol 2000 Hemoglobin A. J. Biol. Chem. 2000, 275:5527-5534.*
Ampulski, R. S., et al., "Determination of the Reactive Sulfhydryl Groups in Heme Proteins with 4,4'-dipyridinedisulfide," Analytical Biochemistry, Oct. 1969, pp. 163-169, vol. 32, No. 1.
Blumenstein, J., et al., "Experimental Transfusion of Dextran-Hemoglobin," Blood Substitutes and Plasma Expanders, 1978, pp. 205-212, vol. 19.
Cosby, K., et al., "Nitrite Reduction to Nitric Oxide by Deoxyhemoglobin Vasodilates the Human Circulation," Nature Medicine, 2003, pp. 1498-1505, vol. 9, No. 12.
Crawford, J. H., et al., "Hypoxia, Red Blood Cells, and Nitrite Regulate NO-Dependent Hypoxic Vasodilation," Blood, 2006, pp. 566-574, vol. 107, No. 2.
Doherty, D. H., et al., "Rate of Reaction With Nitric Oxide Determines the Hypertensive Effect of Cell-Free Hemoglobin," Nature Biotechnology, Jul. 1998, pp. 672-676, vol. 16, No. 7.
Dust, J. M., et al., "Proton NMR Characterization of Poly(ethylene glycols) and Derivatives," Macromolecules, 1990, pp. 3742-3746, vol. 23, No. 16.
Eich, R. F., et al., "Mechanism of NO-Induced Oxidation of Myoglobin and Hemoglobin," Biochemistry, 1996, pp. 6976-6983, vol. 35, No. 22.

(Continued)

*Primary Examiner* — Marcela M Cordero Garcia
*Assistant Examiner* — Jia-Hai Lee
(74) *Attorney, Agent, or Firm* — Senniger Powers LLP

(57) ABSTRACT

PEGylated diaspirin-crosslinked hemoglobin conjugates having high oxygen affinity are described which have enhanced nitrite reductase activity to deliver oxygen, carbon monoxide, nitric oxide or mixtures thereof to tissues to treat various diseases and conditions.

20 Claims, 5 Drawing Sheets

(56) References Cited

OTHER PUBLICATIONS

Furchgott, R. F., "The Role of Endothelium in the Respones of Vascular Smooth Muscle to Drugs," Annual Review of Pharmacology and Toxicology, 1984, pp. 175-197, vol. 24.
Hess, J. R., et al., "Pulmonary and Systemic Hypertension After Hemoglobin Administration," Poster Session IV: Transfusion, Meeting Abstract 1414, Blood, 1991, p. 356A, vol. 78.
Hess, J. R., et al., "Systemic and Pulmonary Hypertension After Resuscitation with Cell-Free Hemoglobin," Journal of Applied Physiology, Apr. 1993, pp. 1769-1778, vol. 74, No. 4.
Huang, Z., et al., "Enzymatic Function of Hemoglobin as a Nitrite Reductase That Produces NO Under Allosteric Control," The Journal of Clinical Investigation, 2005, pp. 2099-2107, vol. 115, No. 8.
Huang, K. T., et al., "The Reaction Between Nitrite and Deoxyhemoglobin. Reassessment of Reaction Kinetics and Stoichiometry," The Journal of Biological Chemistry, 2005, pp. 31126-31131, vol. 280, No. 35.
Hu, T., et al., "Influence of Intramolecular Cross-Links on the Molecular, Structural and Functional Properties of PEGylated Haemoglobin," The Biochemical Journal, Feb. 15, 2007, pp. 143-151, vol. 402, No. 1.
Iwashita, Y., et al., "Renal Toxicity of Hemoglobin Derivatives as Blood Substitute," Organ-Directed Toxicity Chemical Indices and Mechanisms, Proceedings of the Symposium on Chemical Indices and Mechanisms of Organ-Directed Toxicity, Presented in Barcelona, Spain, Mar. 4-7, 1981, pp. 97-101.
Juszczak, L. J., et al., "UV Resonance Raman Study of beta93-modified Hemoglobin A: Chemical Modifier-Specific Effects and Added Influences of Attached Poly(ethylene glycol) Chains," Biochemistry, Jan. 2002, pp. 376-385, vol. 41, No. 1.
Kilbourn, R. G., et al., "Cell-Free Hemoglobin Reverses the Endotoxin-Mediated Hyporesponsivity of Rat Aortic Rings to alpha-adrenergic Agents," Biochemical and Biophysical Research Communications, Feb. 1994, pp. 155-162, vol. 199, No. 1.
Lemon, D. D., et al., "Control of the Nitric Oxide-Scavenging Activity of Hemoglobin," Biotechnology, 1996, p. 378, vol. 24.
Li, D., et al., "Extension Arm Facilitated Pegylation of alphaalpha-hemoglobin with Modifications Targeted Exclusively to Amino Groups: Functional and Structural Advantages of Free Cys-93(beta) in the PEG-Hb Adduct," Bioconjugate Chemistry, Nov. 2009, pp. 2062-2070, vol. 20, No. 11.
Lui, F. E., et al., "Enhancing Nitrite Reductase Activity of Modified Hemoglobin: bis-tetramers and Their PEGylated Derivatives," Biochemistry, Dec. 2009, pp. 11912-11919, vol. 48, No. 50.
Lui, F. E. et al., "Enhancing Nitrite Reductase Activity of Modified Hemoglobin: bis-tetramers and Their PEGylated Derivatives," Thesis submitted to the Graduate Department of Chemistry, University of Toronto, 2011, 102 pages.
Lui, F. E., et al., "Polyethylene Glycol Conjugation Enhances the Nitrite Reductase Activity of Native and Cross-Linked Hemoglobin," Biochemistry, 2008, pp. 10773-10780, vol. 47, No. 40.
Lui, F. E., et al., "Reviving Artificial Blood: Meeting the Challenge of Dealing with NO Scavenging by Hemoglobin," ChemBioChem, 2010, pp. 1816-1824, vol. 11.
MacDonald, V. W., et al., "Vasoconstrictor Effects in Isolated Rabbit Heart Perfused with bis(3,5-dibromosalicyl) Fumarate Cross-Linked Hemoglobin (alpha alpha Hb)," Artificial Cells, Blood Substitutes, and Immobilization Biotechnology, 1994, pp. 565-575, vol. 22, No. 3.
Manjula, B. N., et al., "Cys-93-BetaBeta-Succinimidophenyl Polyethylene Glycol 2000 Hemoglobin A," The Journal of Biological Chemistry, Feb. 25, 2000, pp. 5527-5534, vol. 275, No. 8.
Manjula, B. N., et al., "Conjugation of Multiple Copies of Polyethylene Glycol to Hemoglobin Facilitated Through Tiolation: Influence on Hemoglobin Structure and Function," The Protein Journal, Apr. 2005, pp. 133-146, vol. 24, No. 3.
Muldoon, S. M., et al., "Hemoglobin-Induced Contraction of Pig Pulmonary Veins," The Journal of Laboratory and Clinical Medicine, Dec. 1996, pp. 579-584, vol. 128, No. 6.
Olsen, S., et al., "Correlation Between Hemoglobin Oxygen Affinity and Nitrite Reductase Activity," Meeting Abstract #573.4, The FASEB Journal, 2012, vol. 26, 1 page.
Riess, J. G., "Oxygen carriers ("Blood Substitutes")—raison d'etre, Chemistry, and Some Physiology," Chemical Reviews, Sep. 2001, pp. 2797-2920, vol. 101, No. 9.
Rohlfs, R. J. et al. "Arterial Blood Pressure Responses to Cell-Free Hemoglobin Solutions and the Reaction with Nitric Oxide," The Journal of Biological Chemistry, May 1998, pp. 12128-12134, vol. 273, No. 20.
Tsai, A. G., et al., "Dissociation of Local Nitric Oxide Concentration and Vasoconstriction in the Presence of Cell-Free Hemoglobin Oxygen Carriers," Blood, 2006, pp. 3603-3610, vol. 108, No. 10.
Vandegriff, K. D., et al., "Hemoglobin-Oxygen Equilibrium Binding: Rapid-Scanning Spectrophotometry and Singular Value Decomposition," Methods in Enzymology, 1994, pp. 460-485, vol. 232.
Vandegriff, K. D., et al., "Hemoglobin-Oxygen Equilibrium Curves Measured During Enzymatic Oxygen Consumption," Analytical Biochemistry, Feb. 1998, pp. 107-116, vol. 256, No. 1.
Vandegriff, K. D., et al., "Kinetics of NO and O2 Binding to a Maleimide Poly(ethylene glycol)-conjugated Human Haemoglobin," The Biochemical Journal, Aug. 2004, pp. 183-189, vol. 382, Part 1.
Walder, J. A., et al., "Diaspirins That Cross-Link Beta Chains of Hemoglobin: bis(3,5-dibromosalicyl) Succinate and bis(3,5-dibromosalicyl) Fumarate," Biochemistry, Oct. 1979, pp. 4265-4270, vol. 18, No. 20.
Winslow, R. M., "alphaalpha-Crosslinked Hemoglobin: Was Failure Predicted by Preclinical Testing?" Vox Sanguinis, 2000, pp. 1-20, vol. 79, No. 1.
Winslow, R. M., et al., "Oxygen Equilibrium Curve of Normal Human Blood and Its Evaluation by Adair's Equation," The Journal of Biological Chemistry, Apr. 1977, pp. 2331-2337, vol. 252, No. 7.
Winslow, R. M., et al., "Vascular Resistance and the Efficacy of Red Cell substitutes in a Rat Hemorrhage Model," Journal of Applied Physiology, Sep. 1998, pp. 993-1003, vol. 85, No. 3.
Zalipsky, S., et al., "Attachment of Drugs to Polyethylene Glycols," European Polymer Journal, 1983, pp. 1177-1183, vol. 19, No. 12.

* cited by examiner

DIASPIRIN CROSSLINKED PEGYLATED HEMOGLOBIN

FIELD OF THE INVENTION

The present invention generally relates to crosslinked pegylated hemoglobin and hemoglobin compositions for reducing nitrite to nitric oxide at an enhanced rate in the microvasculature, compared to native hemoglobin. Specifically, the present invention is directed towards using a high oxygen affinity intramolecularly-crosslinked pegylated hemoglobin conjugates having enhanced nitrite reductase activity that can also deliver oxygen, carbon monoxide, nitric oxide, or mixtures thereof to tissues.

BACKGROUND OF THE INVENTION

Hemoglobin-based oxygen carriers ("HBOC") have long been associated with vasoconstriction that has been attributed to nitric oxide (NO) scavenging by heme. Oxygen carriers that are useful as oxygen therapeutics (sometimes referred to as "oxygen-carrying plasma expanders"), such as stabilized hemoglobin (Hb), have been shown to have limited efficacy because they scavenge nitric oxide, causing vasoconstriction and hypertension. The propensity of these oxygen carrying solutions to cause vasoconstriction can manifest as hypertension in animals and man. Although the mechanisms underlying the vasoconstrictive effects of HBOCs are not well understood, it has been suggested that the heme iron may combine rapidly and irreversibly with endogenous NO, a powerful vasodilator, thereby causing vasoconstriction.

In part because of these vasoconstrictive effects, no oxygen carrier to date has been entirely successful as an oxygen therapeutic agent (OTA), although products comprising modified cell-free Hb have been the most promising. Human Hb cross-linked between α-chains with bis-dibromosalicyl-fumarate (ααHb) was developed by the U.S. Army as a model red cell substitute, but was abandoned after it exhibited severe increases in pulmonary and systemic vascular resistance (Hess, J. et al., 1991, Blood 78:356A). A commercial version of this product was also abandoned after a disappointing Phase III clinical trial (Winslow, R. M., 2000, Vox Sang 79:1-20).

Two molecular approaches have been advanced in attempting to overcome the NO binding activity of Hb. The first approach used site-directed mutagenesis of the distal heme pocket in an attempt to create a recombinant hemoglobin with reduced NO-binding affinity (Eich, R. F. et al., 1996, Biochem. 35:6976-83). The second approach used a chemical modification approach wherein the size of the Hb was enhanced through oligomerization in an attempt to reduce or possibly completely inhibit the extravasation of Hb from the vascular space into the interstitial space (Hess, J. R. et al., 1978, J. Appl. Physiol. 74:1769-78; Muldoon, S. M. et al., 1996, J. Lab. Clin. Med. 128:579-83; Macdonald, V. W. et al., 1994, Biotechnology 22:565-75; Furchgott, R., 1984, Ann. Rev. Pharmacol. 24:175-97; and Kilbourne, R. et al., 1994, Biochem. Biophys. Res. Commun. 199:155-62).

In fact, recombinant Hbs with reduced association binding rates for NO have been produced that are less hypertensive in top-load rat experiments (Doherty, D. H. et al. 1998, Nature Biotechnology 16:672-676 and Lemon, D. D. et al. 1996, Biotech 24:378). However, studies suggest that NO binding may not be the only explanation for the vasoactivity of Hb. It has been found that certain large Hb molecules, such as those modified with polyethylene glycol (PEG), were virtually free of vasoconstriction, even though their NO association rates were identical to those of the severely hypertensive ααHb (Rohlfs, R. J. et al. 1998, J Biol. Chem. 273:12128-12134). Furthermore, it was found that PEG-Hb was extraordinarily effective in preventing the consequences of hemorrhage when given as an exchange transfusion prior to hemorrhage (Winslow, R. M. et al. 1998, J. Appl. Physiol. 85:993-1003).

The conjugation of PEG to Hb reduces its antigenicity and extends its circulation half-life. However, the PEG conjugation reaction has been reported to result in dissociation of Hb tetramers into αβ-dimer subunits causing gross hemoglobinuria in exchange-transfused rats receiving PEG-conjugates of Hb monomeric units below 40,000 Daltons ("Da") (Iwashita and Ajisaka Organ-Directed Toxicity: Chem. Indicies Mech., Proc. Symp., Brown et al. 1981, Eds. Pergamon, Oxford, England pgs 97-101). A polyalkylene oxide ("PAO") conjugated Hb having a molecular weight greater than 84,000 Daltons was prepared by Enzon, Inc. (U.S. Pat. No. 5,650,388) that carried about 10 copies of PEG-5,000 chains linked to Hb at its α and ε-amino groups. This degree of substitution was described as avoiding clinically significant nephrotoxicity associated with hemoglobinuria in mammals. However, the conjugation reaction resulted in a heterogeneous conjugate population and contained other undesirable reactants that had to be removed by column chromatography.

PEG conjugation is typically carried out through the reaction of an activated PEG moiety with a functional group on the surface of biomolecules. The most common functional groups are the amino groups of lysine, imidazole groups of histidine residues, and the N-terminus of proteins; thiol groups of cysteine residues; and the hydroxyl groups of serine, threonine and tyrosine residues and the C-terminus of the protein. PEG is usually activated by converting the hydroxyl terminus to a reactive moiety capable of reacting with these functional groups in a mild aqueous environment. One of the most common monofunctional PEGs used for conjugation of therapeutic biopharmaceuticals is methoxy-PEG ("mPEG-OH"), which has only one functional group (i.e. hydroxyl), thus minimizing cross-linking and aggregation problems that are associated with bifunctional PEG. However, mPEG-OH is often contaminated with high molecular weight bifunctional PEG (i.e. "PEG diol"), which can range as high as 10 to 15% (Dust J. M. et al. 1990, Macromolecule 23:3742-3746) due to its production process. This bifunctional PEG diol has roughly twice the size of the desired monofunctional PEG. The contamination problem is further aggravated as the molecular weight of PEG increases. The purity of mPEG-OH is especially critical for the production of PEGylated biotherapeutics, because the FDA requires a high level of reproducibility in the production processes and quality of the final drug product.

Conjugation of Hb to PAOs has been performed in both the oxygenated and deoxygenated states. U.S. Pat. No. 6,844,317 describes conjugating Hb in the oxygenated, or "R" state by equilibrating Hb with the atmosphere prior to conjugation to enhance the oxygen affinity of the resultant PEG-Hb conjugate. Others describe a deoxygenation step prior to conjugation to diminish the oxygen affinity and increase structural stability, enabling the Hb to withstand the physical stresses of chemical modification, diafiltration and/or sterile filtration and pasteurization (U.S. Pat. No. 5,234,903). For intramolecular cross-linking of Hb, it is suggested that deoxygenating Hb prior to modification may be required to expose lysine 99 of the α-chain to the cross-linking reagent (U.S. Pat. No. 5,234,903).

The kinetics of Hb thiolation with 2-iminothiolane prior to conjugation with PEG was investigated by Acharya et al. (U.S. Pat. No. 7,501,499). It was observed that increasing the concentration of iminothiolane from 10-fold, which introduced an average of five extrinsic thiols per tetramer, to 30-fold nearly doubled the number of extrinsic thiols on Hb. However, the size enhancement seen after PEG conjugation was only marginal, even with double the number of thiols. This suggested that the conjugation reaction in the presence of 20-fold molar excess of maleimidyl PEG-5000 covered the surface of the Hb with less reactive thiols, resulting in steric interference that resisted further modification of Hb with more reactive thiols. Consequently, to achieve the desired degree of conjugation of modified Hb (i.e. 6±1 PEG per Hb molecule), Acharya et al. thiolated Hb with an 8-15 fold molar excess of iminothiolane, and then reacted the thiolated Hb with a 16-30 fold molar excess of maleimidyl PEG-5000. However, these high molar excess reactant concentrations in large-scale production significantly increase the cost for preparing the HBOC and increase the heterogeneity of the final product. Moreover, such high molar excess of the maleimidyl PEG-5000 also results in a more heterogeneous product with the production of a greater number of unwanted side reactants.

In previous studies, it was observed that the molecular size of surface modified hemoglobin has to be large enough to avoid being cleared by the kidneys and to achieve the desired circulation half-life. Blumenstein, J. et al., determined that this could be achieved at, or above, a molecular weight of 84,000 Daltons ("Da") ("Blood Substitutes and Plasma Expanders," Alan R. Liss, editors, New York, N.Y., pages 205-212 (1978)). In that study, the authors conjugated dextran of varying molecular weight to Hb. They reported that a conjugate of Hb (with a molecular weight of 64,000 Da) and dextran (having a molecular weight of 20,000 Da) "was cleared slowly from the circulation and negligibly through the kidneys." Further, it was observed that increasing the molecular weight above 84,000 Da did not significantly alter these clearance curves. Intramolecular cross-linking chemically binds together subunits of the tetrameric hemoglobin unit to prevent the formation of dimers which are prematurely excreted by the kidney. (See, e.g., U.S. Pat. No. 5,296,465.

Nitrite reacts with oxyhemoglobin to form methemoglobin, and reacts with deoxyhemoglobin to form methemoglobin and nitric oxide. The vasodilatory effect of nitrite differs from that of traditional NO donors in the presence of hemoglobin and can in part be explained by the nitrite reductase activity of hemoglobin. See Crawford et al. 2006 Blood 107:566-574; Huang et al. 2005 J Biol Chem 280: 31126-31131; Huang et al. 2005 J Clin Invest 115:2099-2107. Studies have shown that nitrite is converted to NO only through reaction with deoxy hemes with the hemoglobin tetramer (Cosby, K. et al. 2003, Nat. Med. 9:1498), and further, that faster reduction of nitrite occurs where the protein heme is in the relaxed or R-state conformation. It is believed that this nitrite reductase activity of hemoglobin is under allosteric control and produces NO at a maximal rate when deoxygenated hemes are in an R-state conformation. R-state stabilizing effects can occur, for example, through modifications at βCys93 sites, such as maleimide PEG conjugation results in increased nitrite reductase activity. Further, it has been shown that while cell-free Hbs caused vasoconstriction and reduced perfusion, MalPEG-Hbs maintained blood flow and microvascular perfusion pressure, which is thought to be related to the lack of vasoconstriction (Tsai, A. G. et al. 2006, Blood 108:3603). Other studies also suggest that the modification of cell-free hemoglobin derivatives with multiple chains of PEG may suppress vasoactivity. Experiments utilizing R-State stabilized Hbs with five to six PEG chains demonstrated 10-fold faster nitrite reductase activity as compared to native Hb (Lui, F. E. et al. 2008, Biochemistry 47(40), 10773-10780). However, it was concluded that any further PEG conjugation at accessible lysine residues did not contribute to increased nitrite reductase activity.

Consequently, there is a need for a method of delivering oxygen, carbon monoxide, nitric oxide, or mixtures thereof to tissue and reducing nitrite to nitric oxide at an enhanced rate in the microvasculature through the use of a high oxygen affinity hemoglobin having increased nitrite reductase properties as compared to existing Hbs.

SUMMARY OF THE INVENTION

In one aspect, the present invention is directed to a β,β-intramolecularly-crosslinked polyoxyalkylene oxide (PAO) hemoglobin conjugate having a P50 ranging from about 2 to 5 mmHg as measured at 37° C. and pH 7.4. The hemoglobin conjugate when fully deoxygenated at 25° C. exhibits a maximal nitrite reductase activity that is at least 10-fold greater than that of deoxygenated stroma-free hemoglobin when measured under the same conditions.

Another aspect of the invention is directed to a β,β-intramolecularly-crosslinked PAO hemoglobin conjugate having a P50 ranging from about 2.0 to 5.0 mmHg as measured at 37° C. and pH 7.4 wherein the hemoglobin conjugate has a maximal nitrite reductase activity of at least 0.25 μM/sec when fully deoxygenated at 25° C.

Yet another aspect of the invention is directed to pharmaceutical compositions comprising the β,β-intramolecularly-crosslinked polyoxyalkylene oxide hemoglobin conjugate and a pharmaceutically acceptable carrier. The compositions can be for use in the treatment of acute liver failure, beta thalassemia, a burn, chronic critical limb ischemia, carbon dioxide or cyanide poisoning, chronic obstructive pulmonary disease (COPD), congestive heart failure, hypoxia, malaria, organ ischemia, peripheral vascular disease, porphyria, pre-eclampsia in pregnancy, sepsis, sickle cell disease, retinal disease, an intra-ocular condition, testicular torsion, trauma, shock, traumatic brain injury, ulcers, vasospasm, or a combination thereof. The compositions can also be for use as an adjunct to angioplasty, as an adjunct for plastic surgery, or as an adjunct in implanting a ventricular assist device; as a blood substitute, a cardioprotectant, a cryopreservative, a hemodialysis adjunct, an oncology agent, an organ preservative, a performance enhancement agent, a surgery adjunct, or a wound healing agent; in imaging; to improve lung function; or a combination thereof. The compositions can also be for veterinary treatment of loss of blood due to injury, hemolytic anemia, infectious anemia, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage, or a combination thereof.

Still another aspect of the invention is directed to a method of treatment comprising administering such a hemoglobin conjugate or pharmaceutical composition to a subject in need thereof. The method is for the treatment of any one or more of the conditions described above.

Another aspect of the invention is directed to a method of delivering oxygen, nitric oxide, carbon monoxide or mixtures thereof to tissue and reducing nitrite to nitric oxide (NO) in the microvasculature. The method comprises administering the β,β-intramolecularly-crosslinked polyoxyalkylene oxide hemoglobin conjugate or the pharmaceutical composition to a subject in need thereof, wherein following administration, the hemoglobin becomes unliganded and converts nitrite to nitric oxide in the microvasculature.

Another aspect of the invention is directed to a method of making the β,β-intramolecularly-crosslinked polyoxyalkylene oxide hemoglobin conjugate as described above. The method comprises the steps of mixing β,β-intramolecularly-crosslinked hemoglobin with 2-iminothiolane (2-IT) in an aqueous diluent to form a thiolated hemoglobin; and adding PAO to the thiolated hemoglobin in the aqueous diluent to form the β,β-intramolecularly-crosslinked polyoxyalkylene oxide hemoglobin conjugate.

Other objects and features will be in part apparent and in part pointed out hereinafter.

BRIEF DESCRIPTION OF THE DRAWINGS

Corresponding reference characters indicate corresponding parts throughout the drawings.

DESCRIPTION OF THE PREFERRED EMBODIMENTS

Figure 1:
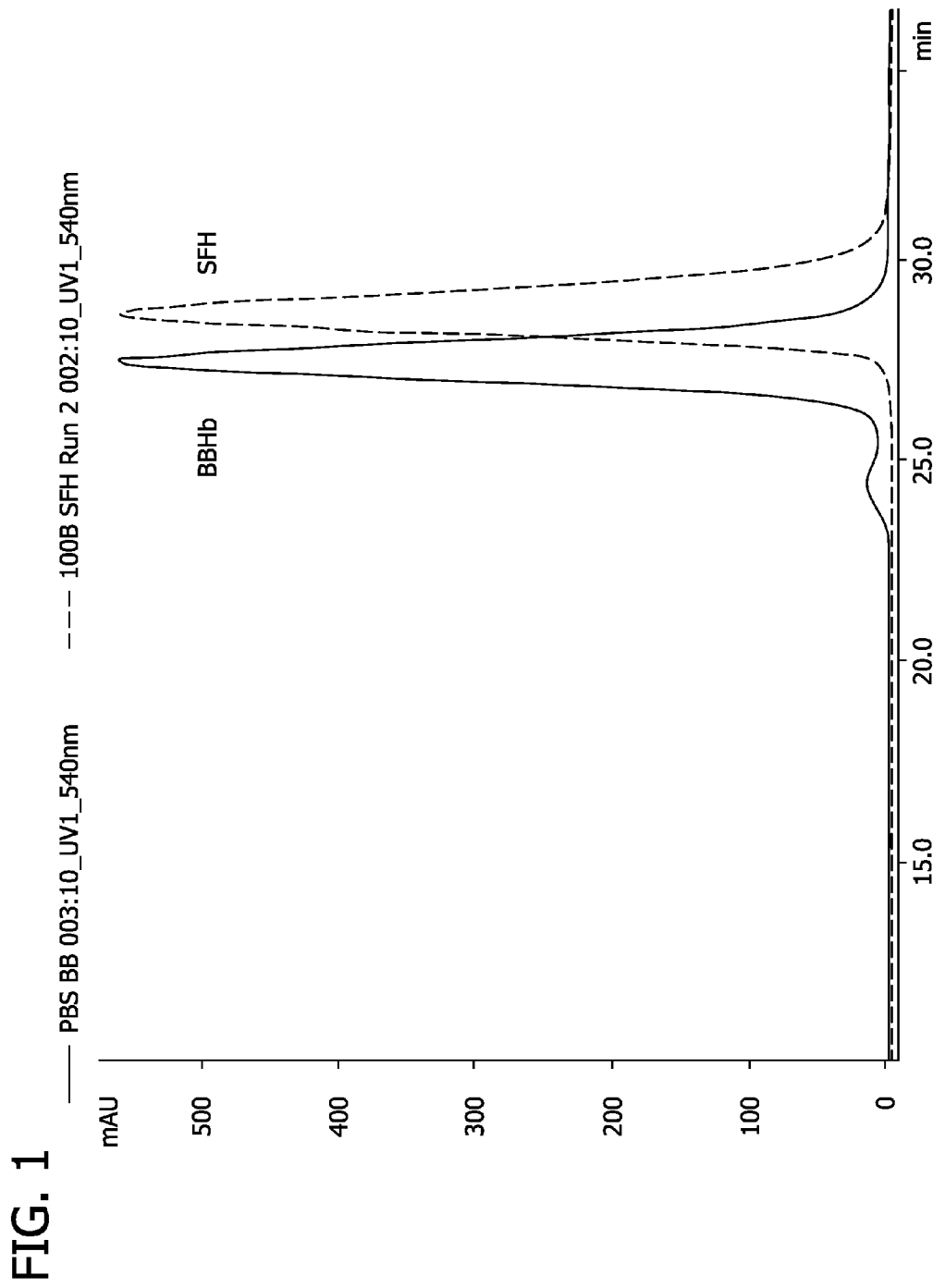
FIG. 1 is a size exclusion chromatogram of stroma free Hb (SFH) (- - -) and ββ-Hb (———) respectively, in non-dissociation condition (PBS), demonstrating confirmation of DBBF crosslinking of ββ-Hb.

β,β-intramolecularly-crosslinked polyoxyalkylene oxide hemoglobin conjugates of high oxygen affinity have been discovered which have enhanced therapeutic properties as compared to conventional hemoglobin therapeutics. These hemoglobin conjugates, when deoxygenated, exhibit a maximal nitrite reductase activity that is at least 10 fold greater than that of deoxygenated stroma-free hemoglobin when measured under the same conditions. The hemoglobin conjugates have a maximal nitrite reductase activity of at least 0.25 μM/s when in fully deoxygenated form at 25° C. The hemoglobin can be delivered in liganded form to deliver oxygen, carbon monoxide or nitric oxide to a subject, and also converts nitrite to nitric oxide in the microvasculature once unliganded.

Without being bound by any particular theory, it is believed that by crosslinking the hemoglobin in the oxygenated, R-state conformation that deoxygenated hemes in the non-dissociable tetramer are locked in a non-flexible R-state that promotes the reduction of nitrite at those deoxy hemes. The unexpectedly much greater nitrite reductase activity of the hemoglobin conjugates of the present invention provides more NO which escapes heme capture and is released from the Hb to the tissue, thereby leading to greater vasodilatory effects compared to other hemoglobin therapeutics. This is believed to occur because the cross-linking of the high-affinity, R-state structure promotes properties within the heme pocket to enhance the reduction of nitrite. Without cross-linking, there is more hemoglobin allosteric conformational change, alternating between T- and R-state heme conformation structures. The cross-linked, fully stabilized R-state structure, even in a deoxygenated heme pocket within the tetramer, is believed to enhance nitrite reduction to NO within the heme pocket.

The present invention is directed to a β,β-intramolecularly-crosslinked polyoxyalkylene oxide (PAO) hemoglobin conjugate having a P50 ranging from about 2 to 5 mmHg as measured at 37° C. and pH 7.4. The hemoglobin conjugate when fully deoxygenated at 25° C. exhibits a maximal nitrite reductase activity that is at least 10-fold greater than that of deoxygenated stroma-free hemoglobin when measured under the same conditions.

The hemoglobin conjugate when fully deoxygenated at 25° C. can exhibit a maximal nitrite reductase activity that is at least 15-fold or at least 20-fold greater than that of deoxygenated stroma-free hemoglobin when measured under the same conditions. Preferably, the hemoglobin conjugate when fully deoxygenated at 25° C. exhibits a maximal nitrite reductase activity that is 10-fold to about 25-fold greater than that of deoxygenated stroma-free hemoglobin when measured under the same conditions, more preferably about 15-fold to about 25-fold greater, 10-fold to about 21-fold greater, or about 15-fold to about 21-fold greater than that of deoxygenated stroma-free hemoglobin when measured under the same conditions.

A β,β-intramolecularly-crosslinked PAO hemoglobin conjugate of the invention can have a P50 ranging from about 2.0 to 5.0 mmHg as measured at 37° C. and pH 7.4 and a maximal nitrite reductase activity of at least 0.25 μM/sec when fully deoxygenated at 25° C. Preferably, the maximal nitrite reductase activity of the hemoglobin conjugate is at least 0.30 μM/sec when fully deoxygenated at 25° C., and more preferably 0.35, 0.40 or 0.45 μM/sec. The maximal nitrite reductase activity of the hemoglobin conjugate can range from 0.25 to about 0.50 μM/sec, or from about 0.30 to about 0.47 μM/sec.

A variety of Hbs may be utilized with the present invention. The Hb may be obtained from animal sources, such as human, bovine, porcine, or equine hemoglobin. Human Hb is preferred. The Hb can be obtained from natural sources or can be produced by known recombinant methods.

The hemoglobin conjugates of the present invention have a high oxygen affinity greater than that of stroma-free hemoglobin. This means that the hemoglobins will have a P50 less than 15 mmHg as measured at 37° C. and pH 7.4, preferably from about 2 to about 5 mmHg, and most preferably from about 2 to about 4 mmHg, or 3 mmHg.

The hemoglobin conjugates can have a colloid osmotic pressure (COP) of at least about 50 mmHg, preferably at least about 60, 65, 70 or 75 mmHg.

The hemoglobins are β,β-intramolecularly crosslinked to prevent dissociation into dimers and to avoid being cleared by the kidneys, extending circulation half-life. Bis(3,5-dibromosalicyl) fumarate (DBBF) crosslinker is used to crosslink two β82 lysine residues of the hemoglobin molecule. Any of the known methods of DBBF crosslinking can be used, such as that described by Walder et al, Biochemistry, 1979; 18(20): 4265-70.

Polyethylene oxides for use in conjugating hemoglobins of the invention include, but are not limited to, polyethylene oxide, polypropylene oxide and a polyethylene/polypropylene oxide copolymer. The PAO has a molecular weight of about 2,000 to about 20,000 Daltons, preferably from about 3,000 to about 10,000 Daltons, more preferably from 4,000 to about 6,000 Daltons, and most preferably about 5,000 Daltons. The most common PAO presently used to modify the surface of Hb is PEG because of its pharmaceutical acceptability and commercial availability. PEG is available in a variety of molecular weights based on the number of repeating subunits of ethylene oxide (i.e. —$CH_2CH_2O$—) within the molecule, to achieve a desired molecular weight based on the number and size of the PEG molecules conjugated to Hb.

The hemoglobins can be conjugated with on average about 7 to about 11 PAO molecules per hemoglobin tetramer. Preferably, the hemoglobins are conjugated to on average about 9 to about 10 PAO molecules per tetramer.

One or both of the terminal end groups of the PAO polymer are converted into a reactive functional group ("activated"). For example, PEG-OH has been used to prepare PEG-halide, mesylate or tosylate, which is then converted to PEG-amine ("PEG-$NH_2$") by performing a nucleophilic displacement reaction with aqueous ammonia (Zalipsky, S. et al., 1983, Eur. Polym. J. 19:1177-1183), sodium azide or potassium phthalimide. The activated PEG can then be conjugated to a heme protein through the interaction of the PEG amine group (—"$NH_2$") with a carboxyl group ("—COOH") of the heme protein.

In addition to functionalizing PEG with an amine group and converting it to a maleimide group, PEGs that are activated therewith, are known to be used in the art. For example, PEG may be activated with p-nitrophenyl carbonate, aldehyde, aminopropyl, aminoethyl, thiol, aminoxy, hydrazide, and iodoacetamide, to name a few. Such functional PEG can be conjugated to the surface amino acid side chains of proteins using known methods.

PEG-$NH_2$ can be further functionalized to conjugate with groups other than carboxyl. For example, U.S. Pat. No. 6,828,401 discloses the reaction of PEG-$NH_2$ with maleimide to form mPEG-maleimide. In this reaction, mPEG-OH is reacted with a tosylating reagent (p-toluenesulfonyl chloride) and a base catalyst (triethyleneamine) in the presence of an organic solvent (dichloromethane) to produce mPEG-tosylate. The mPEG-tosylate is then reacted with 28% ammonia water and maleic acid anhydride in an organic solvent mixture of N, N-dimethylacetamide ("DMAc") and N-cyclohexylpyrrolidinone ("CHP") to produce a maleamic acid compound. This compound is then reacted with pentafluorophenyltrifluoroacetate in the presence of dichloromethane to produce the mPEG-maleimide.

Alternatively, mPEG-maleimide can be made by reacting mPEG-OH with a tosylating reagent (p-toluenesulfonyl chloride) and a base catalyst (triethyleneamine) in the presence of an organic solvent (dichloromethane) to produce mPEG-tosylate. The mPEG-tosylate is then reacted with 28% ammonia to prepare mPEG-$NH_2$. The mPEG-$NH_2$ is then reacted with N-methoxy carbonyl maleimide (MCM) in the presence of saturated sodium hydrocarbonate ($NaHCO_3$) to produce mPEG-maleimide.

Non-limiting examples of amino acid residue side chains of human Hb that can be modified using amine reactive chemistry for conjugation to PAO are presented in Table 1 below:

TABLE 1

Amine Reactive Chemistry and Potential Sites of Modification

| Residues | Positions | Reacts With |
|---|---|---|
| α-chain | | |
| Lys | 7, 11, 16, 40, 56, 60, 61, 90, 99, 127 and 139 | Succinimide; NPC (p-nitrophenyl carbonate); isocyanate; aldehyde; isothiocyanate; epoxides. |
| His | 20, 45, 50, 58, 72, 87, 112 and 122 | Succinimide; NPC (p-nitrophenyl carbonate); isocyanate; aldehyde; isothiocyanate; epoxides. |
| Val | 1 | Succinimide; NPC (p-nitrophenyl carbonate); isocyanate; aldehyde; isothiocyanate; epoxides. |
| β-chain | | |
| Lys | 8, 17, 59, 61, 65, 66, 82, 95, 120, 132 and 144 | Succinimide; NPC (p-nitrophenyl carbonate); isocyanate; aldehyde; isothiocyanate; epoxides. |
| His | 2, 63, 77, 92, 97, 116, 117, 143 and 146 | Succinimide; NPC (p-nitrophenyl carbonate); isocyanate; aldehyde; isothiocyanate; epoxides. |
| Val | 1 | Succinimide; NPC (p-nitrophenyl carbonate); isocyanate; aldehyde; isothiocyanate; epoxides. |

One method to increase the number of available conjugation sites on Hb is to introduce sulfhydryl groups (also known as thiolation), which tend to be more reactive with MalPEG than free amines. A variety of methods are known for protein thiolation. In one method, protein free amines are reacted with succinimidyl 3-(2-pyridyldithio) propionate followed by reduction with dithiothreitol ("DTT"), or tris (2-carboxyethyl)phosphine ("TCEP"). This reaction releases the 2-pyridinethione chromophore, which can be used to determine the degree of thiolation Amines can also be indirectly thiolated by reaction with succinimidylacetylthioacetate, followed by 50 mM hydroxylamine, or hydrazine at near-neutral pH.

Another method described in U.S. Pat. No. 5,585,484 maintains the positive charge of the amino (α- or ε-) group of the Hb after conjugation. This method involves amidination of the ε-amino groups of Hb by 2-IT to introduce sulfhydryl groups onto the protein. This approach has at least two additional advantages over the previously used succinimidyl chemistry: 1) the high reactivity and selectivity of maleimide groups with sulfhydryl groups facilitates the near quantitative modification of the thiols, with a limited excess of reagents and 2) the thiol group of 2-IT is latent and is generated only in situ as a consequence of the reaction of the reagent with the protein amino groups. These advantages provide one additional benefit; they allow simultaneous incubation of Hb with both the thiolating and PEGylation reagent for surface decoration.

For example, MalPEG can be conjugated to Hb by thiolating an amine of the Hb to introduce thiol groups on the surface of the Hb. The two intrinsic thiol groups of Hb that are available for reaction are at βCys93, and added thiol groups on the surface of the Hb can react with the maleimide of the maleimidyl PAO to form a pegylated Hb conjugate.

The polyalkylene oxide can be covalently attached via a thiol reactive moiety to a thiol group of an exposed amino acid side chain on the hemoglobin molecule while the hemoglobin is in the oxygenated state.

The maleimide-PEG can be conjugated to a thiol moiety of the hemoglobin selected from an intrinsic thiol moiety of a cysteine residue of the hemoglobin, a thiol moiety of a thiolated lysine residue of the hemoglobin, or a combination thereof.

The maleimide-PEG includes a linker to attach the maleimide to the PEG. Linkers can include, but are not limited to, alkylene such as ethylene, propylene, or isopropylene, phenylene, amide (—NH—C(O)—), or phenyl carbamate (e.g., -Ph-NH—C(O)—). Preferably, the polyalkylene oxide is linked to the thiol reactive moiety by a linker consisting of alkylene or phenylene, and more preferably alkylene such as ethylene.

The maleimide-PEG can have the structure

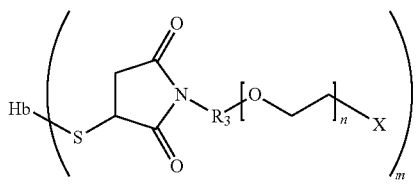

wherein Hb is hemoglobin, S is a thiol of the hemoglobin, $R_3$ is an alkylene or phenylene group, X is a terminal group, m is the average number of maleimidyl-activated PEG polymers conjugated to the hemoglobin, and n is the average number of oxyethylene units of a PEG having an average molecular weight of about 2,000 to about 20,000 Daltons. Preferably, $R_3$ is an alkylene such as ethylene; X is hydroxy, aryloxy such as benzyloxy, or $C_1$-$C_{20}$ alkoxy, more preferably $C_1$-$C_{10}$ alkoxy group, and still more preferably a $C_1$-$C_5$ alkoxy group such as methoxy or ethoxy; n is from about 3,000 to about 10,000 Daltons, more preferably from 4,000 to about 6,000 Daltons, and most preferably about 5,000 Daltons; and m is about 7 to about 11, and more preferably about 9 or about 10.

Non-limiting examples of amino acid residue side chains that can be modified using thiol reactive chemistry are presented in Table 2 below:

TABLE 2

Thiol Reactive Chemistry and Potential Sites of Modification

| Residues | Positions | Reacts With |
|---|---|---|
| α-chain | | |
| Cys | 104 | Maleimide; iodoacetamide; orthopyridyl-disulfide (OPSS); vinylsulfone. |
| β-chain | | |
| Cys | 93 and 112 | Maleimide; iodoacetamide; orthopyridyl-disulfide (OPSS); vinylsulfone. |

The two intrinsic thiols at the βCys93 residues of hemoglobin can be pegylated or can be reacted with N-ethyl maleimide. Such modification of these cysteine residues decreases P50, and has R-state stabilizing effects.

The molecular weight of the PAO-Hb can be regulated by the conjugation reaction. Conventional thought suggested that increasing the molar ratios of the reactants would increase the number of PEG molecules bound to Hb. This included both the thiolation process of Hb (i.e. increasing the molar ratio of thiolating agent to Hb) and the conjugation process (i.e. increasing the molar ratio of thiol activated PEG to thiolated Hb). However, these excess molar ratios resulted in the binding of only 6±1 PEG molecules per Hb (see U.S. Pat. No. 7,501,499).

Recently it was determined that a greater number of PAO molecules could be bound to Hb using lower molar ratios of reactants. The number of available thiol groups on Hb, before and after thiolation and after conjugation, was determined using the dithiopyridine colorimetric assay (Ampulski, R. S. et al., 1969, Biochem. Biophys. Acta 32:163-169). Human Hb contains two intrinsic, reactive thiol groups at the β93 cysteine residues, which was confirmed by the dithiopyridine reaction. After thiolation of SFH with 2-IT, the number of reactive thiol groups increased from two to over seven. In this example, an average of 8 PEG molecules was bound to Hb. This was achieved using a 7.5-fold molar excess of 2-IT over SFH in the thiolation reaction and a 12-fold molar excess of MalPEG over thiolated Hb in the conjugation reaction.

Hemoglobin is conjugated with polyalkylene oxide when it is in the oxygenated state to increase the oxygen affinity of the Hb-PAO conjugate.

Thus, another aspect of the invention is directed to a method of making the hemoglobin conjugate. The method comprises the steps of: mixing β,β-intramolecularly-crosslinked hemoglobin with 2-iminothiolane (2-IT) in an aqueous diluent to form a thiolated hemoglobin; and adding PAO to the thiolated hemoglobin in the aqueous diluent to form the β,β-intramolecularly-crosslinked polyoxyalkylene oxide hemoglobin conjugate.

In this method, the 2-iminothiolane is present at a concentration of between about 8- and about 25-fold molar excess over the hemoglobin concentration, preferably about 15-fold molar excess.

The thiolation can be performed at a pH of about 7 to about 9.

The conjugation can be performed at a pH of about 7 to about 9.

In this method, the PAO-maleimide is present at a concentration of between about 10- to about 40-fold molar excess over the hemoglobin concentration based on 100% terminal activity, preferably about 28-fold molar excess.

The hemoglobin conjugates of the invention can be in oxygenated or deoxygenated form, can be liganded to CO or NO, or can be a mixture including two or more of these four forms. $HbO_2$ is prepared by equilibrating non-oxygenated hemoglobin with air, pure $O_2$ gas or $O_2$/nitrogen gas mixtures.

Deoxygenation can be performed by any method known in the art. One simple method is to expose the hemoglobin solution to an inert gas, such as nitrogen, argon or helium. To assure that deoxygenation is relatively homogeneous, the Hb solution is circulated in this process. Monitoring deoxygenation to attain desired levels may be performed by using a Co-oximeter 682 (Instrument Laboratories). If partial reoxygenation is desired, deoxygenated Hb may be exposed to oxygen or to a gas mixture containing oxygen, such as air.

Gas exchange to replace molecular oxygen with another gas may be accomplished through a gas-permeable membrane, such as a polypropylene or cellulose acetate membrane. See, for example, published U.S. Patent Application No. 2006/0234915. Commercially available gas-exchange devices utilizing these membranes include the Celgard™ polypropylene microporous hollow fiber device from Hoechst-Celanese (Dallas, Tex.) or the Cell-Pharm™ hollow fiber oxygenator from American Laboratory (East Lyme, Conn.). In the Hoechst-Celanese Celgard™ device, oxygenated Hb is deoxygenated by passing an aqueous Hb solution through polypropylene microporous hollow filters at 10-100 ml/min/ft$^2$ while the system is purged with nitrogen at 5-20 psi. The Hb is generally circulated for about 5 to 30 minutes to achieve the desired percentage of deoxyHb. Another method for producing deoxygenated Hb comprises exposing a Hb solution to a chemical reducing agent such as sodium ascorbate, sodium dithionate and sodium bisulfite. Hb is partially deoxygenated by adjusting the reducing agent concentration, reaction time and temperature. Alternatively, a reducing agent may be used to substantially deoxygenate Hb, and then oxygen may be reintroduced to form a partially deoxygenated product. For example, Hb can be exposed to a 100 mM concentration of sodium bisulfite for about one hour before adding antioxidants.

Hb can be liganded to CO using any known methods for forming oxyhemoglobin, simply by substituting CO for $O_2$. This generally involves introducing a source of CO to a solution of hemoglobin such that the hemoglobin becomes liganded with CO instead of $O_2$ (K. D. Vandegriff, et al., Biochem. J. 382:183-189 (2004)). Since hemoglobin has a higher affinity for CO than it does for oxygen, it is not necessary to first deoxygenate the hemoglobin. Accordingly, the most convenient way of forming CO-Hb complexes is by introducing 100% gaseous CO to a solution of hemoglobin.

HbNO can be prepared by reacting deoxygenated hemoglobin with nitric oxide gas, or by exposing CO-Hb to NO gas such that the NO exchanges for CO. HbNO can also be made by reacting deoxygenated hemoglobin with a small NO-donor molecule like PROLI NONOate™ (i.e., 1-(hydroxy-NNO-azoxy)-L-proline, disodium salt; Cayman Chemical, Ann Arbor, Mich.).

It should be noted that hemoglobin to which NO, a free radical, is bound to the amino acid side groups in the globin chain are not NO-Hb complexes as defined herein, since such compounds do not contain diatomic (nonionic) NO as a ligand in the heme pocket instead of oxygen. For example, nitrosylhemoglobin is formed when native hemoglobin is exposed to a NO donor under conditions that cause it to bind to free sulfhydryl groups (U.S. Pat. No. 6,627,738). Such nitrosylhemoglobins still carry oxygen, whereas the NO-Hb complexes of the present invention do not. Furthermore, when the modified hemoglobin is formed by a reaction directed towards sulfhydryl moieties such as described above, these moieties are no longer available for NO binding.

The PAO-Hb conjugates of the present invention can be formulated as a pharmaceutical composition comprising the PAO-Hb conjugate in a pharmaceutically acceptable carrier for parenteral administration, such as an aqueous diluent. The concentration of the PAO-Hb conjugate in the carrier can vary according to the application. Preferably, the PAO-Hb conjugate concentration ranges from about 0.1 g/dl to about 10 g/dl, more preferably from about 2.0 g/dl to about 8.0 g/dl, and most preferably about 4.0 to about 6.0 g/dl. The selection of an appropriate concentration of hemoglobin depends on the colloidal osmotic (oncotic) properties of the final hemoglobin product. Preferably, the compositions of the invention can be normo-oncotic as compared to whole blood or hyperoncotic as compared to plasma. The hemoglobin concentration can be adjusted to obtain the desired oncotic pressure for each indication.

When the composition is formulated as a parenteral, the solution generally comprises a physiologically compatible electrolyte carrier isosmotic with whole blood and which maintains the reversible oxygen-, CO- or NO-carrying and delivery properties of the hemoglobin.

The pharmaceutically acceptable carrier can be an aqueous diluent. The aqueous diluent can comprise an aqueous solution of a colloid or an aqueous solution of a non-oxygen carrying component, such as an aqueous solution of proteins such as albumin, an aqueous solution of glycoproteins, an aqueous solution of polysaccharides, or a combination thereof. The aqueous diluent can comprise an aqueous cell-free solution.

Suitable aqueous diluents include, but are not limited to, physiological saline, a saline-glucose mixture, Ringer's solution, lactated Ringer's solution, Locke-Ringer's solution, Krebs-Ringer's solution, Hartmann's balanced saline, heparinized sodium citrate-citric acid-dextrose solution, an acetate solution, a multiple electrolyte solution (e.g., Plasma Lyte® or Plasma Lyte-A® from Baxter International, Deerfield, Ill.), a lactobionate solution, and polymeric plasma substitutes, such as polyethylene oxide, polyvinyl pyrrolidone, polyvinyl alcohol, an ethylene oxide-propylene glycol condensate, or a combination thereof.

The composition can additionally comprise pharmaceutically-acceptable fillers, salts, and other materials well-known in the art, the selection of which depends on the dosage form, the condition being treated, the particular purpose to be achieved according to the determination of the ordinarily skilled artisan in the field and the properties of such additives. For example, the composition can include physiological buffers, carbohydrates (e.g. glucose, mannitol, or sorbitol), alcohols or poly alcohols, pharmaceutically acceptable salts (e.g., sodium or potassium chloride), surfactants (e.g., polysorbate 80), anti-oxidants, anti-bacterial agents, oncotic pressure agents (e.g. albumin or polyethylene glycols) or reducing agents (e.g., ascorbic acid, glutathione, or N-acetyl cysteine).

The pharmaceutical compositions have a viscosity of at least about 2 centipoise (cP). More specifically, the viscosity ranges from about 2 to about 5 cP, and particularly about 2.5 to about 4.5 cP.

In order to avoid complications in administration, the pharmaceutical composition is of high purity, i.e. free from stroma, phospholipids, and pyrogens, having an endotoxin level of no more than 0.25 EU/ml, as measured by the LAL (limulus amebocyte lysate) test, and having less than 8% methemoglobin.

Pharmaceutical compositions can be administered parenterally, such as by subcutaneous, intravenous, or intramuscular injection, or as large volume parenteral solutions. The compositions can also be administered by gavage.

A typical dose of hemoglobin conjugate as a therapeutic agent can be from about 1 to about 15,000 milligrams of hemoglobin per kilogram of patient body weight. For example, when used as an oxygen therapeutic, the dosage will range between 100 to 7500 mg/kg patient body weight, more preferably 500 to 5000 mg/kg body weight, and most preferably 700 to 3000 mg/kg body weight. Thus, a typical dose for a human patient might be from a gram to over 1000 grams. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

The PAO-Hb conjugates and pharmaceutical compositions can be used to deliver oxygen, CO and/or NO to a subject. A method of delivering oxygen, nitric oxide, carbon monoxide or mixtures thereof to tissue and reducing nitrite to produce further endogenous nitric oxide (NO) in the microvasculature includes administering the hemoglobin conjugate or the composition to a subject in need thereof, wherein following administration, the hemoglobin becomes unliganded and converts nitrite to nitric oxide in the microvasculature.

The hemoglobin conjugates and compositions thereof of the invention can be used: to treat acute liver failure, beta thalassemia, a burn, chronic critical limb ischemia, carbon dioxide or cyanide poisoning, chronic obstructive pulmonary disease (COPD) (e.g., acute exacerbations), congestive heart failure (e.g., acute heart failure, chronic heart failure), hypoxia (e.g., high altitude use including for pulmonary edema, decompression sickness), malaria (e.g., cerebral malaria (Falciparum occlusive events), organ ischemia (e.g., acute bowel ischemia (torsion), acute bowel ischemia (embolism), cardiogenic shock, acute vascular organ ischemia, stroke (before CAT scan), stroke (after CAT scan), myocardial infarction/severe cardiac ischemia), peripheral vascular disease, porphyria, pre-eclampsia in pregnancy, sepsis, sickle cell disease (e.g., stroke/transient ischemic attack, splenic sequestration, hepatic sequestration, priapism), retinal disease/intra-ocular condition (e.g., central retinal artery occlusion, central venous occlusion), testicular torsion, trauma/shock (e.g., traumatic hemorrhagic shock, non-traumatic hemorrhagic shock, pre-hospital/field use (military/emergency), traumatic brain injury/blast), ulcers, or vasospasm; as an adjunct to angioplasty, as an adjunct for plastic surgery (skin flaps) (e.g., acute treatment, chronic treatment), or as an adjunct in implanting a ventricular assist device; as a blood substitute (e.g., for acute blood loss, Jehovah's Witness, difficult to cross-match patient, rare blood group, sickle aplastic crisis, sickle cell anemia perioperative management, acute hemolytic anemia (autoimmune), acute hemolytic anemia (toxin), or other refractory anemia), a cardioprotectant, a cryopreservative, a hemodialysis adjunct, an oncology agent (e.g., adjunct to radiotherapy or chemotherapy, solid tumors), an organ preservative (e.g., ex vivo, in donor, in recipient), a performance enhancement agent (e.g., civilian/athletic, military), a surgery adjunct (e.g., cardiopulmonary bypass (prime), cardiopulmonary bypass (adjustment), lung ischemia, pre-surgery conditioning, ruptured aortic aneurysm, replacement of thoracic aorta (dissection or aneurysm)), or a wound healing agent; in imaging (x-ray or magnetic resonance imaging (MRI)); to improve lung function (e.g., acute lung injury, chronic lung injury, transient viral pneumonia, neonatal distress syndrome); or a combination thereof. Such uses include administration of the conjugate or composition to a subject in need thereof.

Further, the hemoglobins and compositions of the invention can be used to treat non-traumatic hemorrhagic shock, pre-hospital setting trauma, traumatic hemorrhagic shock, acute lung injury, adult respiratory distress syndrome, traumatic brain injury, stroke, solid tumor cancer, organ degradation (ex-vivo), organ degradation (in recipient), severe sepsis/septic shock, myocardial infarction/cardiac ischemia, cardiogenic shock, acute heart failure, pulmonary embolism, various conditions by surgery (e.g., adjunct to angioplasty, adjunct to thoracic aortic repairs, adjunct to cardiopulmonary bypass, priming solution for cardiopulmonary bypass), or a combination thereof.

The numerous clinical settings in which the hemoglobins and compositions of the present invention are useful include the following:

Trauma.

An acute loss of whole blood can result in a fluid shift from the interstitial and intracellular spaces to replace the lost volume of blood while shunting of blood away from the low priority organs including the skin and gut. Shunting of blood away from organs reduces and sometimes eliminates $O_2$ levels in these organs and results in progressive tissue death. The primary goal is to oxygenate affected tissues. This trauma can be in a pre-hospital setting or can result in traumatic hemorrhagic shock or traumatic brain injury.

Ischemia.

The conjugates and compositions thereof can also be used to deliver oxygen, CO, and/or NO to areas that red blood cells or many other oxygen therapeutics cannot penetrate. These areas can include any tissue areas that are located downstream of obstructions to red blood cell flow, such as areas downstream of thrombi, sickle cell occlusions, arterial occlusions, angioplasty balloons, surgical instrumentation, and any tissues that are suffering from oxygen starvation or are hypoxic. All types of tissue ischemia can be treated including, for example, stroke, emerging stroke, transient ischemic attacks, myocardial stunning and hibernation, acute or unstable angina, emerging angina, infarct, and the like. In particular, conditions resulting in ischemia include acute heart failure, cardiogenic shock, myocardial infarction/cardiac ischemia, stroke, pulmonary embolism, non-traumatic hemorrhagic shock, or cerebrovascular trauma.

Hemodilution.

In this application, the therapeutic is administered to replace (or substitute for) the $O_2$ levels of the removed autologous blood. This permits the use of the removed autologous blood for necessary transfusions during and after surgery. One such surgery requiring pre-operative blood removal would be a cardiopulmonary bypass procedure.

Sepsis/Septic Shock.

In sepsis, some patients may become hypertensive in spite of massive fluid therapy and treatment with vasoconstrictor agents. In this instance, the overproduction of nitric oxide (NO) results in lowered blood pressure. Therefore hemoglobin is a desirable agent for treatment of these patients because hemoglobin binds NO with a high avidity.

Hypoxemia.

When a patient has acute lung injury caused by either pneumonia or pancreatitis, hypoxemia can be observed and can be alleviated by providing the hemoglobins or compositions of the invention to oxygenate the affected tissues.

Cancer.

Delivery of $O_2$ to the hypoxic inner core of a solid tumor mass increases its sensitivity to radiotherapy and chemotherapy. Because the microvasculature of a tumor is unlike that of other tissues, sensitization through increasing $O_2$ levels requires $O_2$ be unloaded within the hypoxic core. In other words, the P50 should be very low to prevent early unloading of the $O_2$, increasing the $O_2$ levels, to insure optimal sensitization of the tumor to subsequent radiation and chemotherapy treatments.

Surgery.

The hemoglobins and compositions of the invention can be used during various surgical procedures. For example, they can be used as an adjunct to angioplasty, thoracic aortic repairs, during a cardiopulmonary bypass procedure or as a cardiopulmonary priming solution.

Organ Perfusion.

During the time an organ is maintained ex vivo or in an organ donation recipient, maintaining $O_2$ content helps preserve structural and cellular integrity and minimizes infarct formation. The hemoglobins and compositions can sustain the oxygen requirements for such an organ.

The hemoglobins and compositions thereof can also be used in non-humans, such as domestic animals (e.g., livestock and companion animals such as dogs, cats, horses, birds, reptiles. It is contemplated that the present invention finds utility in the emergency treatment of domestic and wild animals suffering a loss of blood due to injury, hemolytic anemias, etc. Veterinary uses include treatment of loss of blood due to injury, hemolytic anemia, infectious anemia, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage.

Definitions

When the terms "one," "a" or "an" are used in this disclosure, they mean "at least one" or "one or more," unless otherwise indicated.

"Activated polyalkylene oxide" or "activated PAO" as used herein refer to a PAO molecule that has at least one functional group. A functional group is a reactive moiety that interacts with free amines, sulfhydryls or carboxyl groups on a molecule to be conjugated with PAO. For example, one such functional group that reacts with free sulfhydryls is a maleimide group. A functional group that reacts with free amines is a succinimide group.

"Deoxyhemoglobin" or "unliganded hemoglobin" means any hemoglobin to which no exogenous ligand is bound to heme.

"Hemoglobin" or "Hb" refers generally to a heme protein that transports oxygen. In humans, each molecule of Hb has 4 subunits, 2α-chain subunits and 2β-chain subunits, which are arranged in a tetrameric structure. Each subunit also contains one heme group, which is the iron-containing center that in the ferrous ($Fe^{2+}$) binds the ligands $O_2$, NO or CO. Thus, each Hb molecule can bind up to 4 ligand molecules, making $HbO_2$, HbNO, or HbCO liganded compounds, respectively. Additionally, the hemoglobin may be liganded with mixtures of $O_2$, NO and CO.

"Hemoglobin based oxygen carriers" (HBOCs) refers to hemoglobins that carry oxygen, but are also useful for carrying other molecular gases, such as carbon monoxide and nitric oxide.

"High oxygen affinity" refers to hemoglobin that has been modified to exhibit an oxygen affinity greater than that of stroma free-hemoglobin (SFH). Thus, a "high oxygen affinity" Hb has a P50 less than that of SFH, which has a P50 of 15 mmHg as measured at 37° C. and pH 7.4.

"Liganded hemoglobin" means hemoglobin to which an exogenous ligand is bound to heme. Common preferred ligands include oxygen, carbon monoxide, and nitric oxide.

"MalPEG" refers to maleimidyl polyethylene glycol, and includes a maleimidyl moiety attached to polyethylene glycol via a linker.

"MalPEG-Hb" refers to Hb to which maleimidyl-activated PEG has been conjugated. The conjugation is performed by reacting MalPEG with thiol groups (and to a lesser extent, amino groups) on the Hb to form MalPEG-Hb. Thiol groups are found in cysteine residues present in the amino acid sequence of Hb, such as the two intrinsic thiols at βCys 93, and can also be introduced by modifying surface amino groups to contain a thiol group. An exemplary MalPEG-Hb known as MP4 (Sangart, Inc.) has the following formula:

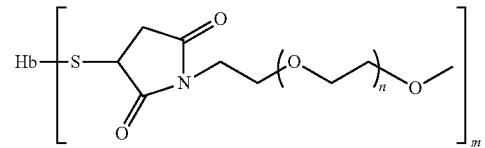

wherein Hb is hemoglobin; S is a thiol group on the hemoglobin; n is the number of oxyethylene units of the 5,000-Dalton polyalkylene oxide polymer; and m is the average number of maleimidyl-activated polyalkylene oxide polymers conjugated to the hemoglobin and is 7-8.

"Methemoglobin" or "metHb" refer to an oxidized form of Hb that contains iron in the ferric state. MetHb does not function as an oxygen or CO carrier. The term "methemoglobin %" as used herein refers to the percentage of oxidized Hb to total Hb.

"Methoxy-PEG" or "mPEG-OH" refer to PEG wherein the hydrogen of the hydroxyl terminus is replaced with a methyl ($—CH_3$) group.

"Modified hemoglobin" or "modified Hb" refers to Hb that has been altered by a chemical reaction, such as intra- and inter-molecular crosslinking, polymerization, conjugation, and/or recombinant techniques, such that the Hb is no longer in its "native" state. As used herein, the terms "hemoglobin" or "Hb" refer to both native unmodified Hb and modified Hb, unless otherwise indicated.

"Nitrite reductase activity" or "NRA" is the ability of hemoglobin or a hemoglobin-based protein to reduce nitrite to nitric oxide. "Maximal nitrite reductase activity" is the maximum rate that hemoglobin or a hemoglobin-based protein is able to reduce nitrite to nitric oxide. "Initial nitrite reductase activity" is the initial rate that hemoglobin or a hemoglobin-based protein reduces nitrite to nitric oxide when nitrite is added to the fully deoxygenated protein.

The term "non-oxygenated" means that the heme protein or hemoglobin is in the non-liganded, deoxygenated state, or it is liganded with a gas other than $O_2$, such as NO or CO.

"Oxygen affinity" refers to the avidity with which an oxygen carrier, such as Hb, binds molecular oxygen. This characteristic is defined by the oxygen equilibrium curve, which relates the degree of saturation of Hb molecules with oxygen (Y axis) with the partial pressure of oxygen (X axis). The position of this curve is denoted by the "P50" value, which is the partial pressure of oxygen at which the oxygen carrier is half-saturated with oxygen, and is inversely related to oxygen affinity. Hence, the lower the P50, the higher the oxygen affinity. The oxygen affinity of whole blood (and components of whole blood, such as red blood cells and Hb) can be measured by a variety of methods known in the art. (see, e.g., Winslow, R. M. et al., J. Biol. Chem. 1977, 252:2331-37). Oxygen affinity may also be determined using a commercially available HEMOX™ Analyzer (TCS Scientific Corporation, New Hope, Pa.). (see, e.g., Vandegriff and Shrager in "Methods in Enzymology" (Everse et al., eds.) 232:460 (1994)); and Vandegriff, et al., Anal. Biochem. 256(1): 107-116 (1998)).

The term "oxygen therapeutic agent" as used herein refers to a heme protein that is capable of binding to and carrying molecular oxygen to cells/tissues/organs in need thereof. When administered in the form of a CO- or NO-liganded heme protein, once the CO or NO is released from the heme moiety, the heme groups are then free to bind to and carry molecular oxygen.

"Polyethylene glycol" or "PEG" refer to a polymer of the general chemical formula $H(OCH_2CH_2)_nOH$ where "n" is greater than or equal to 4, preferably about 45 to about 500, more preferably about 70 to about 250, and most preferably about 90 to about 140, or about 115. The polymer can be substituted or unsubstituted, and the terminal hydroxy group can be replaced with a different conventional terminal group, such as methoxy or carboxy. PEGs are commercially available from many sources (e.g., Carbowax™ (Dow Chemical, Midland, Mich.), Poly-G® (Arch Chemicals, Norwalk, Conn.) and Solbase).

"Polyethylene glycol-conjugated hemoglobin," "PEG-Hb conjugate" or "PEG-Hb" refer to Hb to which at least one PEG is covalently attached.

"Solution" refers to a liquid mixture and the term "aqueous solution" refers to a solution that contains some water and may also contain one or more other liquid substances with water to form a multi-component solution.

"Stroma-free hemoglobin" or "SFH" refer to Hb from which red blood cell membranes have been removed.

"Surface-modified hemoglobin" refers to hemoglobin to which chemical groups, usually polymers, have been attached, such as dextran or polyalkylene oxide. The term "surface-modified oxygenated hemoglobin" refers to Hb that is in the "R" state when it is surface modified.

"Terminal activity" is an indication of the percentage of PAO that is functionalized with a moiety capable of reacting with a reactive group of the heme protein or hemoglobin. "100% Terminal activity" indicates that the molar excess of the PAO used in the conjugation reaction is expressed on a basis that all of the PAO has a moiety capable of reacting with a reactive group of the heme protein or hemoglobin. For example, if an available Mal-PEG has 80% terminal activity such that 80% of the PEGs are functionalized with Mal, and the Mal-PEG is used in 20-fold molar excess over hemoglobin, then this molar ratio can be expressed as a 16-fold molar excess of Mal-PEG over hemoglobin based on 100% terminal activity.

"Thiolation" refers to a process that increases the number of sulfhydryl groups on a molecule. For example, reacting a protein with 2-iminothiolane ("2-IT") converts free amines on the surface of the protein to sulfhydryl groups. These sulfhydryl groups are then available for reaction with a thiol reactive moiety, such as a maleimide.

"Unliganded hemoglobin" refers to any hemoglobin containing at least one heme moiety that is not liganded to a molecular gas such as oxygen, carbon monoxide or nitric oxide. As such, the hemoglobin is considered "unliganded" if only one of the heme moieties is not liganded to a molecular gas.

All publications, patents, and patent applications cited in this specification are incorporated herein by reference for the subject matter specifically referenced herein as if each such publication, patent or patent application were specifically and individually indicated to be incorporated herein by reference.

Having described the invention in detail, it will be apparent that modifications and variations are possible without departing from the scope of the invention defined in the appended claims.

EXAMPLES

The following non-limiting examples are provided to further illustrate the present invention.

Example 1: Preparation of PEGylated ββ-DBBF-Crosslinked Hemoglobin Conjugate

Packed red blood cells ("RBCs") are procured from a commercial source, such as from a local Blood Bank, the New York Blood Center, or the American Red Cross. The material is obtained not more than 45 days from the time of collection. All units are screened for viral infection and subjected to nucleic acid testing prior to use. Non-leukodepleted pooled units are leukodepleted by membrane filtration to remove white blood cells. Packed RBCs are pooled into a sterile vessel and stored at 2-15° C. until further processing. The volume is noted, and Hb concentration is determined using a commercially available co-oximeter, or other art-recognized method.

RBCs are washed with six volumes of 0.9% sodium chloride using a 0.45-μm tangential flow filtration, followed by cell lysis by decreasing the concentration of salt. Hb extraction is performed using the same membrane. The cell wash is analyzed to verify removal of plasma components by a spectrophotometric assay for albumin. The lysate is processed through a 0.16-μm membrane in the cold to purify Hb. The purified Hb is collected in a sterile depyrogenated and then ultrafiltered to remove virus. Additional viral-reduction steps, including solvent/detergent treatment, nanofiltration, and anion Q membrane purification may be performed. All steps in this process are carried out at 2-15° C.

Hb from lysate is exchanged into Ringer's lactate ("RL"), or phosphate-buffered saline ("PBS", pH 7.4), using a 30-kD membrane. The Hb is concentrated to 1.1-1.5 mM (in tetramer). Ten to 12 volumes of RL or PBS are used for solvent exchange. This process is carried out at 2-15° C. The pH of the solution prepared in RL or PBS is adjusted to 8.0 prior to thiolation. The Hb is sterile-filtered through a 0.45 or 0.2-μm disposable filter capsule and stored at 4±2° C. before the chemical modification reaction is performed.

Crosslinking:

ββ-DBBF crosslinked Hb was prepared by reaction of stroma-free hemoglobin (SFH) prepared from packed red blood cells with bis(3,5-dibromosalicyl)fumarate (DBBF) as described previously by Walder et al, Biochemistry, 1979; 18(20): 4265-70. Oxygenated SFH in borate buffer (pH~8.5) was reacted with two fold molar excess of DBBF for about 16 hours at about 2-8° C.

Thiolation:

Using the SFH prepared as described above, thiolation was carried out using a 15-fold molar excess of 2-iminothiolane (2-IT) over Hb. The ratio and reaction time were optimized to maximize the number of thiol groups for PEG conjugation and to minimize product heterogeneity. Approximately 1 mM Hb (tetramer) in RL (pH 7.0-8.5), PBS or any similar buffer, was combined with 15 mM 2-IT in the same buffer. This mixture was continuously stirred for about 6 hours at 10±5° C.

The dithiopyridine colorimetric assay (Ampulski, R. S. et al., Biochem. Biophys. Acta 1969, 32:163-169) was used to measure the number of available thiol groups on the surface of the Hb tetramer before and after thiolation, and then again after Hb-PEG conjugation. Human Hb contains two intrinsic reactive thiol groups at the β93 cysteine residues, which was confirmed by the dithiopyridine reaction. After thiolation of SFH at a ratio of 1:<8 (SFH: 2-IT), the number of reactive thiol groups increased from two to greater than seven thiols.

PEG Conjugation:

MalPEG was conjugated to the thiolated ββ-DBBF cross-linked Hb using a 28-fold molar excess of MalPEG based on 100% terminal activity over the starting tetrameric Hb concentration. The Hb was first allowed to equilibrate with the atmosphere to oxygenate the Hb. Approximately 1 mM thiolated Hb in RL (pH 7.0-8.5), PBS or any similar buffer was combined with 28 mM MalPEG in the same buffer. This mixture was continuously stirred for about 6 hours at 10±5° C.

The resulting PEG-Hb conjugate was processed through a 70-kD membrane (i.e. <0-volume filtration) to remove unreacted reagents. This process was monitored by size-exclusion liquid chromatography ("LC") at 540 nm and 217 nm. The concentration was adjusted to 4.4 g/dl Hb and the pH was adjusted to 6.0±7.8.

The PEG-Hb conjugate was sterile filtered using a 0.2-μm sterile disposable capsule and collected into a sterile depyrogenated vessel at 4±2° C. The PEG-Hb conjugate was diluted to 4.4 g/dl RL and the pH adjusted to 7.4±0.2 pH and then sterile-filtered (0.2 μm) and aliquoted into endotoxin free sterile containers.

The final PEGylated ββ-DBBF crosslinked hemoglobin conjugate ("PEG-ββ-Hb") had the properties shown in Table 3:

TABLE 3

Properties of PEG-ββ-Hb

| Properties | Values |
|---|---|
| Hb Concentration (g/dL) | 4.4 |
| pH | 7.4 |
| Degree of PEGylation | 7.6 |
| COP (mmHg) | 85 |
| P50 mmHg | 2.6 |
| Hill number (n-value) | 1.05 |

Figure 2:
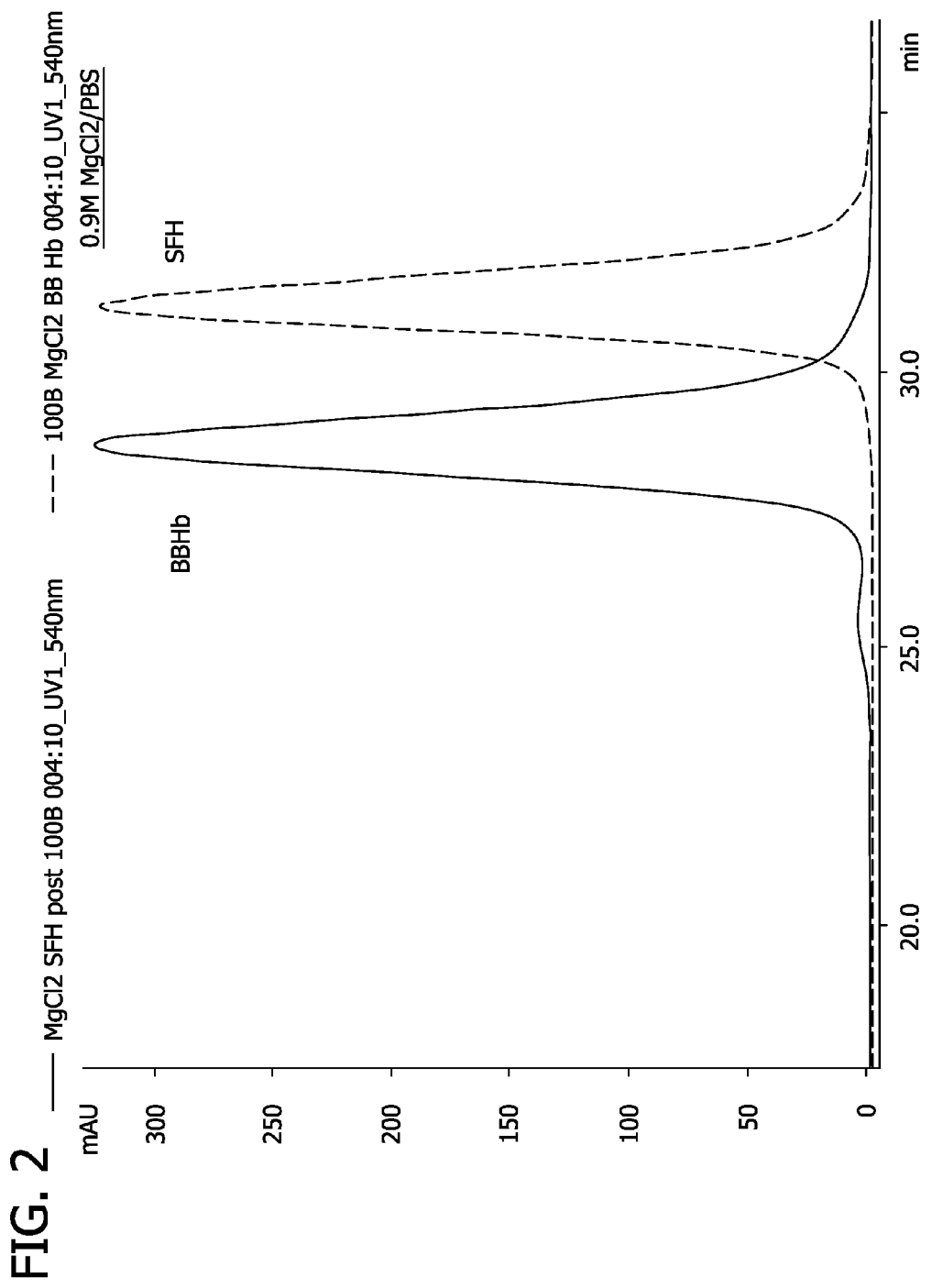
FIG. 2 is a size exclusion chromatogram a size exclusion chromatogram of stroma free Hb (SFH) (- - -) and ββ-Hb (———) respectively, in dissociation condition (PBS), demonstrating confirmation of DBBF crosslinking of ββ-Hb.
Figure 3:
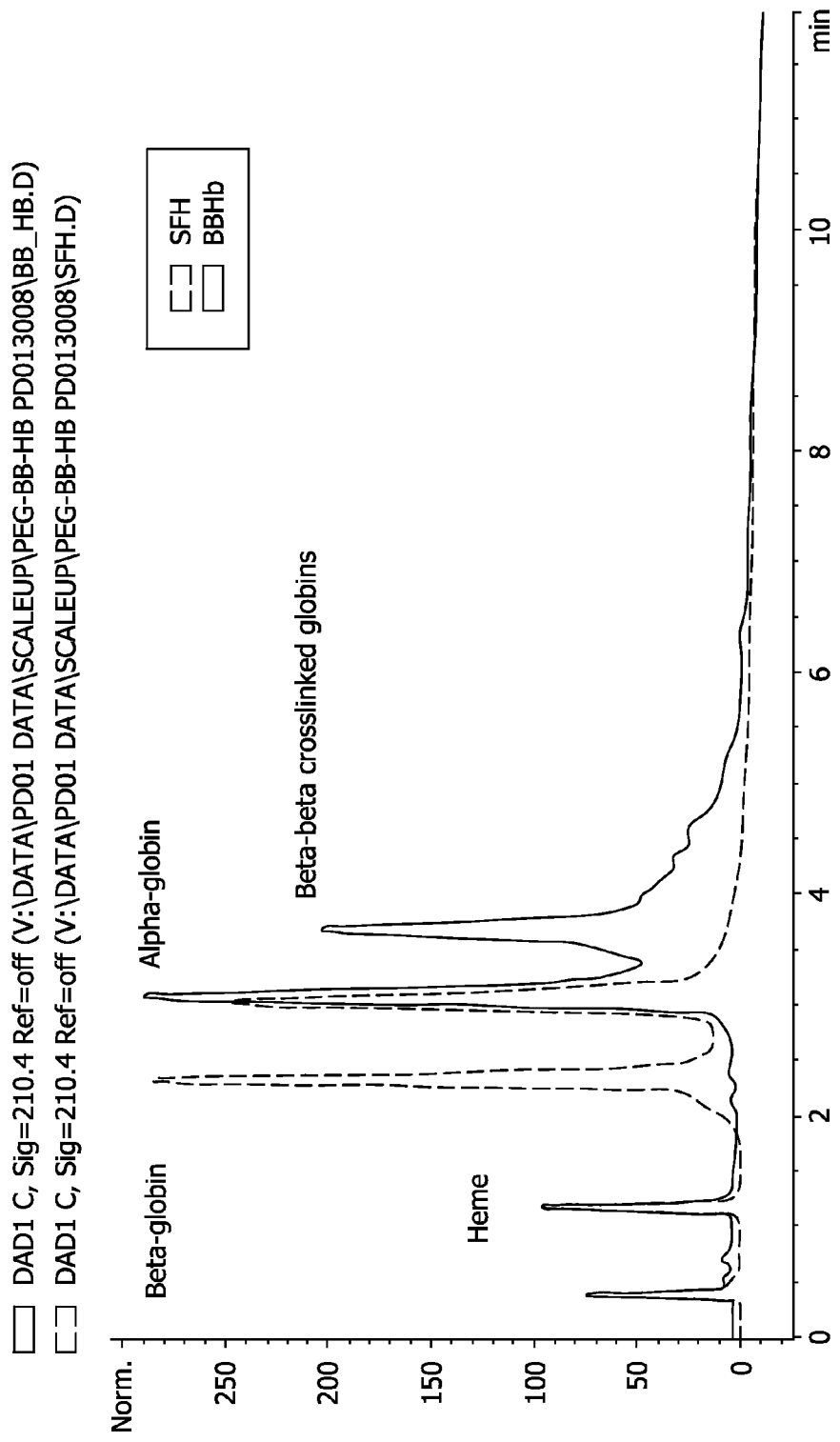
FIG. 3 is a reverse-phase high performance liquid chromatogram demonstrating the confirmation of DBBF crosslinking of the β-subunits wherein (SFH) (- - -) and ββ-Hb (———) respectively.
Figure 4:
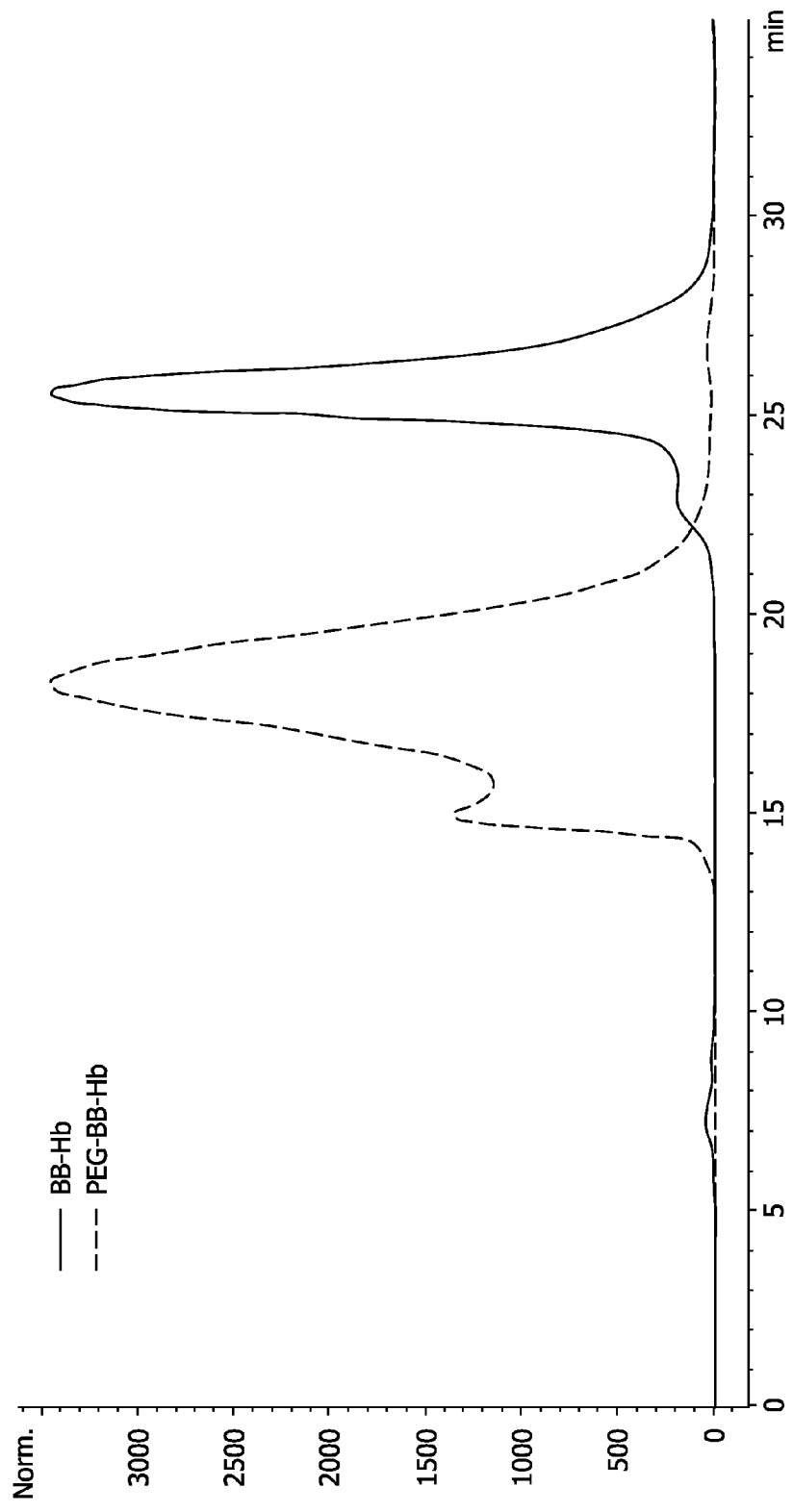
FIG. 4 a size exclusion chromatogram of PEG-ββ-Hb (- - -) and ββ-Hb (———) respectively, in non-dissociation condition, demonstrating PEGylation of PEG-ββ-Hb.

The structure of PEG-ββ-Hb was further confirmed via standard methodology. Size exclusion chromatography confirmed the presence of DBBF crosslinking (FIGS. 1 and 2). Reverse-phase high performance liquid chromatography confirmed the presence of DBBF crosslinking of the β globin subunits of the hemoglobin (FIG. 3). The PEGylation of ββ-DBBF Hb was confirmed using size exclusion chromatography (FIG. 4).

Example 2: Enhanced Nitrite Reductase Activity Exhibited by PEG-ββ-Hb

Deoxygenated PEGylated ββ-DBBF-crosslinked hemoglobin from Example 1 and other hemoglobin species for comparison purposes were reacted anaerobically with sodium nitrite in a sealed cuvette in the presence of sodium dithionite. A ten-fold excess of nitrite was used over heme, and the reaction was monitored spectrophotometrically. The resulting spectral data were deconvoluted using parent spectra for deoxyhemoglobin, iron-nitrosyl-hemoglobin, and methemoglobin. The rates were plotted as the derivative of the disappearance of deoxyhemoglobin and the maximum rates were used for comparison purposes.

SFH and PEGylated ββ-DBBF-crosslinked hemoglobin reduced nitrite to NO with maximum rates of 0.0215 μM/s and 0.462 μM/s, respectively, showing a 21-fold higher maximum rate for PEGylated ββ-DBBF-crosslinked hemoglobin compared to SFH.

Figure 5:
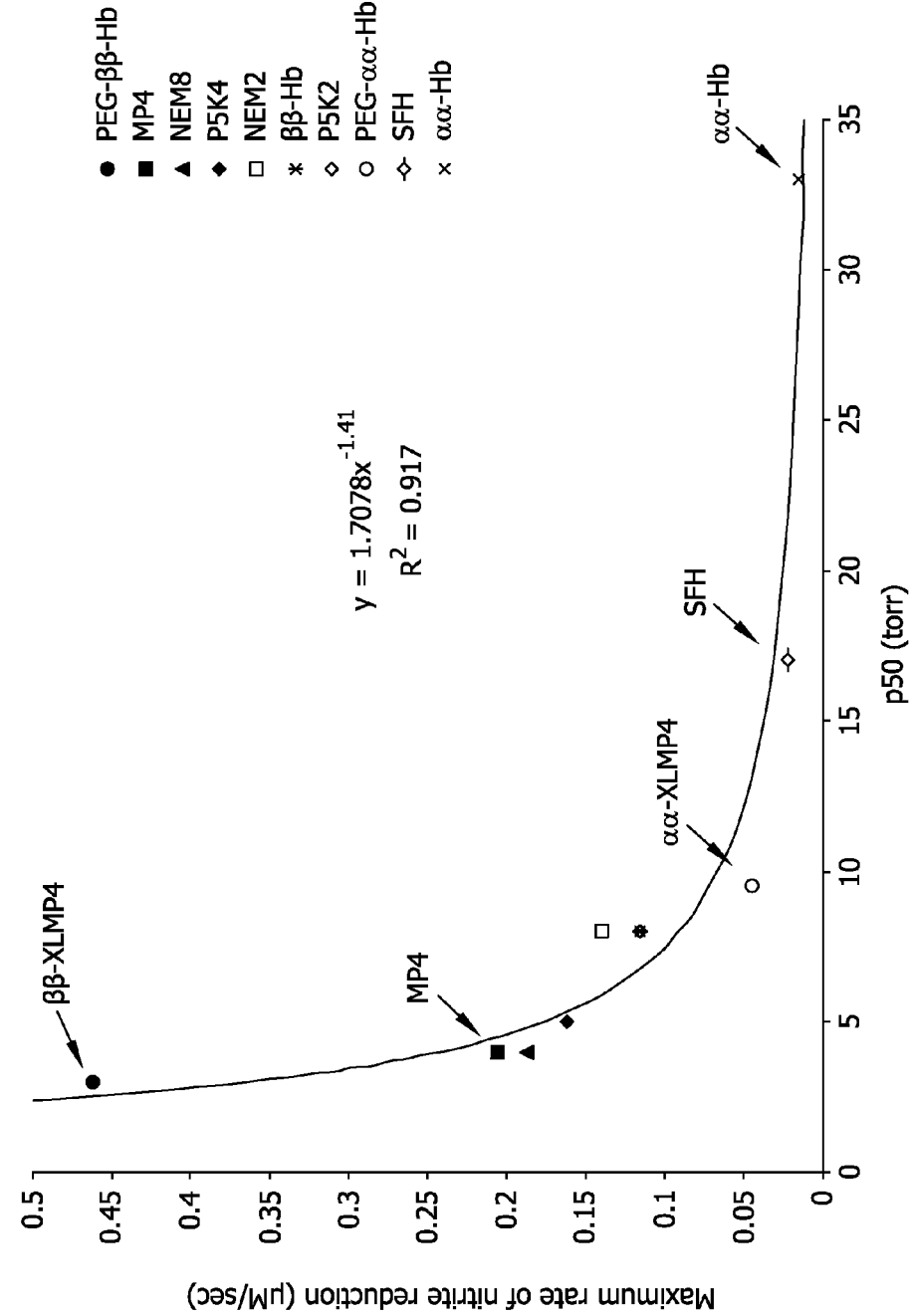
FIG. 5 is a graphical depiction of the nitrite reductive properties of various hemoglobins.

Referring to FIG. 5, nitrite reductase activity of several types of modified Hbs were determined, including maleimide-conjugated non-crosslinked hemoglobin, which reacts at Hb β93Cys residues to decrease P50. Maleimides tested include the small molecule, N-ethylmaleimide (NEM), and MP4 (Sangart, Inc.) as well as the other hemoglobins specified in Table 4.

TABLE 4

Properties of Modified Hemoglobins

| Hb | Conjugation Chemistry | Degree of Substitution per Tetramer | P50 (oxygen affinity) |
|---|---|---|---|
| SFH | N/A | — | 16 |
| MP4OX | Maleimide | 8 (PEG 5K) | 4 |
| P5K2 | Maleimide | 2 (PEG 5K) | 8 |
| P5K4 | Maleimide | 4 (PEG 5K) | 5 |
| NEM2 | Maleimide | 2 (NEM) | 9 |
| NEM8 | Maleimide | 8 (NEM) | 5 |
| SVA-PEG-Hb | Succinimide | Not tested | 7 |
| αα-Hb | DBBF | — | 33 |
| ββ-Hb | DBBF | — | 8 |
| PEG-αα-Hb | DBBF/Maleimide | 7 (PEG 5K) | 9 |
| PEG-ββ-Hb | DBBF/Maleimide | 7.6 (PEG 5K) | 3 |

Hbs cross-linked between α or β subunits exhibit varying P50. The P50 values ranged from 3 mmHg (for PEG-ββ-Hb) to 33 mmHg (for αα-crosslinked Hb). It was observed that there is a direct correlation between P50 and nitrite reductase activity. Hbs with high oxygen affinity (low P50) reduced nitrite to NO at a higher rate than low affinity Hbs. With a 10-fold excess of nitrite, the maximum rate of nitrite reduction varied from 0.46 μM/s (for PEG-ββ-Hb) to 0.015 μM/s (for αα-crosslinked Hb). NO produced by this reaction can escape heme capture and be released from Hb, and the rate of NO release is relative to the nitrite reductase activity. Together, these results suggest that oxygen affinity is important in cell-free Hb design, not only to enhance the delivery of hemoglobin ligands, but also to maximize nitrite reductase activity.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A β,β-intramolecularly-crosslinked polyalkylene oxide hemoglobin tetramer conjugate having a P50 ranging from about 2 to 5 mmHg as measured at 37° C. and pH 7.4, wherein the hemoglobin conjugate when fully deoxygenated at 25° C. exhibits a maximal nitrite reductase activity that is at least 10-fold greater than that of deoxygenated stroma-free hemoglobin when measured under the same conditions, wherein the hemoglobin is conjugated to on average about 7 to about 11 polyalkylene oxide molecules per tetramer.

2. The hemoglobin conjugate of claim 1, wherein the maximal nitrite reductase activity of the hemoglobin conjugate is at least 0.25 µM/sec when fully deoxygenated at 25° C.

3. The hemoglobin conjugate of claim 2 wherein the maximal nitrite reductase activity ranges from 0.25 to about 0.50 µM/sec.

4. The hemoglobin conjugate of claim 1 wherein the polyalkylene oxide is covalently attached via a thiol reactive moiety to a thiol group of an exposed amino acid side chain on the hemoglobin molecule while the hemoglobin is in the oxygenated state.

5. The hemoglobin conjugate of claim 4 wherein the polyalkylene oxide is linked to the thiol reactive moiety by a linker consisting of alkylene or phenylene.

6. The hemoglobin conjugate of claim 1 wherein the hemoglobin is bis(3,5-dibromosalicyl) fumarate crosslinked at two β82 lysine residues of the hemoglobin molecule.

7. The hemoglobin conjugate of claim 1 wherein colloid osmotic pressure is at least 75 mmHg, the P50 is about 2 to about 4 mmHg.

8. The hemoglobin conjugate of claim 1 wherein the hemoglobin conjugate is liganded to oxygen, carbon monoxide, or nitric oxide, or is deoxygenated.

9. The hemoglobin conjugate of claim 1, wherein the PAO is a polyethylene glycol (PEG) having an average molecular weight of about 2,000 to about 20,000 Daltons.

10. The hemoglobin conjugate of claim 9, wherein the PEG is a maleimide-PEG, and the maleimide is linked to the PEG via an alkylene or phenylene linker.

11. The hemoglobin conjugate of claim 10, wherein the alkylene linker is an ethylene linker.

12. The hemoglobin conjugate of claim 10, wherein the maleimide-PEG is conjugated to a thiol moiety of the hemoglobin selected from an intrinsic thiol moiety of a cysteine residue of the hemoglobin, a thiol moiety of a thiolated lysine residue of the hemoglobin, or a combination thereof.

13. The hemoglobin conjugate of claim 1, wherein N-ethyl maleimide is conjugated to β93 cysteine residues of the hemoglobin.

14. The hemoglobin conjugate of claim 10, wherein the maleimide-PEG has the structure

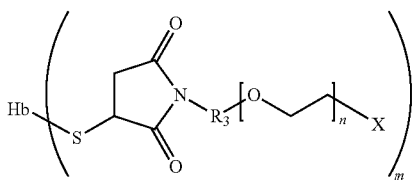

wherein:
Hb is hemoglobin,
S is a thiol of the hemoglobin,
$R_3$ is an alkylene or phenylene group,
X is hydroxy, aryloxy, or $C_1$-$C_{20}$ alkoxy,
m is about 7 to about 11, and
n is the average number of oxyethylene units of a PEG having an average molecular weight of about 2,000 to about 20,000 Daltons.

15. The hemoglobin conjugate of claim 14, wherein $R_3$ is ethylene; X is methoxy or ethoxy; n is the average number of oxyethylene units of a PEG having an average molecular weight of about 3,000 to about 10,000 Daltons; and m is about 9 or about 10.

16. A pharmaceutical composition comprising the β,β-intramolecularly-crosslinked polyalkylene oxide hemoglobin conjugate of claim 1 and a pharmaceutically acceptable carrier.

17. A method of treatment comprising administering a hemoglobin conjugate of claim 1 to a subject in need thereof, wherein either:
the method is a method for the treatment of acute liver failure, beta thalassemia, a burn, chronic critical limb ischemia, carbon dioxide or cyanide poisoning, chronic obstructive pulmonary disease (COPD), congestive heart failure, hypoxia, malaria, organ ischemia, peripheral vascular disease, porphyria, pre-eclampsia in pregnancy, sepsis, sickle cell disease, retinal disease, an intra-ocular condition, testicular torsion, trauma, shock, traumatic brain injury, ulcers, vasospasm, or a combination thereof; or
the method is a method for the treatment of non-traumatic hemorrhagic shock, pre-hospital setting trauma, traumatic hemorrhagic shock, acute lung injury, adult respiratory distress syndrome, traumatic brain injury, stroke, solid tumor cancer, organ degradation (ex-vivo), organ degradation (in recipient), severe sepsis, septic shock, myocardial infarction, cardiac ischemia, cardiogenic shock, acute heart failure, pulmonary embolism, or a combination thereof; or
the hemoglobin tetramer is administered as an adjunct to angioplasty, as an adjunct for plastic surgery, or as an adjunct in implanting a ventricular assist device; as a blood substitute, a cardioprotectant, a cryopreservative, a hemodialysis adjunct, an oncology agent, an organ preservative, a performance enhancement agent, a surgery adjunct, or a wound healing agent in imaging; to improve lung function; or a combination thereof; or
the hemoglobin tetramer is administered as an adjunct to thoracic aortic repairs, as an adjunct to cardiopulmonary bypass, or as a priming solution for cardiopulmonary bypass; or
the subject is a non-human animal and the method is a method for veterinary treatment of loss of blood due to injury, hemolytic anemia, infectious anemia, bacterial infection, Factor IV fragmentation, hypersplenation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic anemia, parasitism, or surgical-anesthesia induced brain damage.

18. A method of delivering oxygen, nitric oxide, carbon monoxide or mixtures thereof to tissue and reducing nitrite to nitric oxide (NO) in the microvasculature, the method comprising administering the β,β-intramolecularly-crosslinked polyalkylene oxide hemoglobin conjugate of claim 1 to a subject in need thereof, wherein following administration, unliganded hemes in the hemoglobin convert nitrite to nitric oxide in the microvasculature.

19. A method of making the β,β-intramolecularly-crosslinked polyalkylene oxide hemoglobin conjugate of claim 1, the method comprising the steps of:
mixing β,β-intramolecularly-crosslinked hemoglobin with 2-iminothiolane (2-IT) in an aqueous diluent to form a thiolated hemoglobin; and
adding PAO to the thiolated hemoglobin in the aqueous diluent to form the β,β-intramolecularly-crosslinked polyalkylene oxide hemoglobin conjugate.

20. A β,β-intramolecularly-crosslinked polyalkylene oxide hemoglobin conjugate having a P50 ranging from about 2 to 5 mmHg as measured at 37° C. and pH 7.4, wherein the hemoglobin conjugate when fully deoxygenated at 25° C. exhibits a maximal nitrite reductase activity that is at least 10-fold greater than that of deoxygenated stroma-free hemoglobin when measured under the same conditions, the β,β-intramolecularly-crosslinked polyalkylene oxide hemoglobin conjugate having the formula:

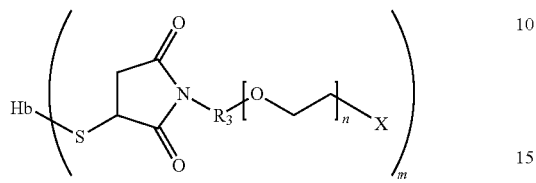

wherein:
Hb is a hemoglobin bis(3,5-dibromosalicyl) fumarate crosslinked at two (382 lysine residues of the hemoglobin molecule,
S is a thiol of the hemoglobin,
$R_3$ is an alkylene or phenylene group,
X is hydroxy, aryloxy, or $C_1$-$C_{20}$ alkoxy,
m is about 7 to about 11, and
n is the average number of oxyethylene units of a PEG having an average molecular weight of about 2,000 to about 20,000 Daltons.

* * * * *